United States Patent [19]
Gonzalez et al.

[11] Patent Number: 6,071,516
[45] Date of Patent: Jun. 6, 2000

[54] TREATMENT OF POST-POLIO SYNDROME WITH GAMMA-GLOBULIN

[75] Inventors: Henrik Gonzalez, Stockholm; Kristian Borg, Taby, both of Sweden

[73] Assignee: Pharmalink Baslakemedel AB, Sweden

[21] Appl. No.: 09/285,125

[22] Filed: Apr. 1, 1999

[51] Int. Cl.$^7$ ................ A61K 39/42; A61K 39/395; C07K 16/00

[52] U.S. Cl. ................ 424/130.1; 424/159.1; 530/389.4

[58] Field of Search ................ 424/130.1, 159.1; 530/389.4

[56] References Cited

PUBLICATIONS

Stiehm, RE Pediatrics 63:301–319, 1979.
Dwyer, N.E. Journal of Medicine 326:107–116, 1992.
Annonymous, Health after 50, Johns Hopkins Newsletter, JHMI, Baltimore MD, p. 8, 1999.
Dinsmore, S. et al. Annals of the NY Academy of Sciences 753:303–313, 1995.
Salazar–Gruezo et al., Comprehensive Therapy 16:24–30, 1990.

*Primary Examiner*—David Saunders
*Assistant Examiner*—Amy DeCloux
*Attorney, Agent, or Firm*—Ostrolenk, Faber, Gerb & Soffen, LLP

[57] ABSTRACT

A method for treating a patient suffering from Post-Polio Syndrome (PPS) comprises the intravenous, intramuscular or subcutaneous administration of a pharmacologically effective amount of an immunomodulating agent, in particular gamma-globulin. Also disclosed is the use of the immunomodulating agent for the manufacture of a corresponding medicament, and a pharmaceutical composition for treatment of PPS comprising gamma-globulin.

12 Claims, No Drawings

TREATMENT OF POST-POLIO SYNDROME WITH GAMMA-GLOBULIN

FIELD OF THE INVENTION

The present invention relates to a method for treating Post-Polio Syndrome (PPS) and to a pharmaceutical composition useful in this treatment.

BACKGROUND OF THE INVENTION

The Post-Polio Syndrome (PPS) is a condition encountered in persons having had a poliomyelitis infection earlier in their life. PPS appears after a long stable period of several decades following acute polio infection. It is generally characterized by increased or new muscle weakness, muscle atrophy, muscle fatigue, and pain. The cause of PPS has not yet been established. Autopsy of PPS patients who died of other diseases reveals inflammatory cells in the spinal cord. Also, non-specific inflammatory changes have been shown to occur in their cerebrospinal fluid.

Several mechanisms have been proposed for the pathogenesis of PPS, including attrition of motor neurons because of aging or persistent remnants of poliovirus, and an activated immunoresponse.

While there is no curative treatment of PPS pain related to PPS may be alleviated, albeit not very efficiently, by administering analgesics. There is thus a great need for a method for treating PPS.

OBJECTS OF THE INVENTION

It is an object of the present invention to provide a method for treating PPS.

It is another object of the invention to provide a pharmaceutical composition for such treatment.

Further objects of the invention will be apparent from the following description.

SUMMARY OF THE INVENTION

The invention is based on the finding that patients with PPS show abnormally increased levels of major histocompatibility complex (MHC) expressing interleukin-4 (IL-4) m-RNA levels in their cerebrospinal fluid (CSF) in particular, but also abnormally increased levels of interleukin-10 (IL-10) m-RNA, gamma-interferon (IF$\gamma$) m-RNA, and tumor necrosis factor-alpha (TNF$\alpha$) m-RNA. These levels differ statistically significantly from those found in healthy volunteers. This indicates that there might be an ongoing inflammation in the CSF of PPS patients. Other findings by the inventors furthermore indicate that inflammation in PPS patients is restricted to CSF.

IL-4 is an inflammatory cytokine produced by antigen-presenting cells and type 2 T-helper cells. IL-4 is a mediator between T-lymphocytes and B-lymphocytes involved in the stimulation of antibodies and/or antibody-mediated immunity, potentiated by the complement system and PMNs. The complicated interactions between inflammatory cells and also between different mediators in the inflammatory cascade are not fully understood. When these mediators act within the central nervous system interpretation is complicated by the fact that CNS immunologically differs from other organs and peripheral tissues. Normally the brain-blood barrier allows only few immunocompetent cells to pass, restricting even the passage of antibodies and immunomediators. T-cells in the peripheral circulation can reach CNS only if activated. The T-cells do not have to be activated against a specific antigen to pass the barrier. This mechanism, called "immune surveillance", enables T-cells to find specific antigens or pathogens in the cells and then to become specifically activated. The cells of the CNS also show low expression of MHC major histocompatibility antigens. In the CNS, MHC expression thus might be induced by trauma, infections or autoimmune reactions.

In PPS patients, the inventors found abnormal amounts of mononuclear cells expressing mRNA for IL-4 indicating an abnormal immunoresponse but also of cells expressing abnormally increased levels of IL-10 m-RNA, IF$\gamma$ m-RNA, and TNF$\alpha$ m-RNA. Other neuroinflammatory parameters, such as IgG-index, CSF-protein, CSF/serum albumin ratio, and total CSF cell counts were however not found to deviate from normal in the same patients. This indicates a chronic immunological imbalance sustained by persistent remnants of an old poliomyelitis infection as, for instance, mutated poliovirus. The abnormal counts of T-cells expressing m-RNA coding for IL-4, but also T-cells expressing m-RNA coding for IL-10, IF$\gamma$, and TNF$\alpha$, could indicate such a persistent infection by poliomyelitis virus, and a chronic inflammatory process resulting therefrom.

These findings do however not preclude that reported episodes of the deteriorating health status of PPS patients might be due to other events, such as infection by virus other than poliomyelitis virus. Such infection might non-specifically activate T-cells, enabling them to enter CNS. There they might become more specifically antigenically activated, their action being directed against cells of the cornu anterius medullae spinalis. Again, the result might be a chronic inflammatory process.

Whereas these findings and hypotheses are only given for explanation and must not be considered to limit the present invention in any way, they induced the present inventors to conceive an immunomodulatory treatment for Post-Polio Syndrome patients.

In accordance with the present invention is disclosed a method for treating a patient suffering from Post-Polio Syndrome (PPS) comprising the intravenous, intramuscular or subcutaneous administration of a pharmacologically effective amount of an immunomodulating agent. Preferably administration is intravenous. It is preferred for the immunomodulating agent to be gamma-globulin, in particular 'normal' gamma-globulin, that is, gamma-globulin produced from human plasma collected from large number of donors and pooled prior to fractionation.

It is preferred for the daily dose of gamma-globulin to be from 0.01 g/kg/day to 1.0 g/kg/day, preferably from about 0.1 g–0.4 g/kg/day. A preferred single daily dose comprises from 0.5 g to 50.0 g gamma globulin. It is preferred for a treatment period to be from 1 to 6 days, or even up to two weeks. After a treatment-free period, a second treatment period may follow, and so on. Preferably the treatment-free period is at least one day, more preferred at least three days, most preferred at least two weeks. According to the invention thus is disclosed a treatment scheme comprising a plurality of treatment periods interrupted by treatment-free periods of a combined length preferably greater than that of the treatment periods. Some patients may however benefit from a continuous treatment extending over longer periods of time, such a month or more, or even of a life-long uninterrupted treatment.

In accordance with the present invention is also disclosed a pharmaceutical composition for intravenous, intramuscular or subcutaneous administration for the treatment of Post-Polio Syndrome (PPS) comprising a pharmacologically effective amount of 'normal' gamma-globulin and a carrier.

Furthermore, in accordance with the present invention is disclosed the manufacture of a medicament for intravenous administration for the treatment of Post-Polio Syndrome comprising a pharmacologically effective amount of gamma globulin, in particular 'normal' gamma-globulin, and a pharmaceutically acceptable carrier.

The invention will now be described in more detail by reference to a preferred but not limiting embodiment.

Other features and advantages of the present invention will become apparent from the following description of the invention which refers to the accompanying drawings.

EXAMPLE 1

Non-PPS Specific Laboratory Data From PPS Patients and Healthy Controls

Inclusion criteria: PPS patients with elevated levels of MNC with expression of mRNA coding for IL-4 and/or other cytokines. Exclusion criteria: Selective IgA deficiency.

The PPS group comprised 13 patients which were compared with a group of seven healthy volunteers.

Peripheral blood (PB) was obtained from venous blood sample and CSF by lumbar puncture. For both groups plasma electrophoresis was performed, and levels of alpha-1-antitrypsin, orosomucoid, haptoglobin, IgA, IgG, IgM and Complement factors 3 and 4 (as C3d) were measured in peripheral blood. The CSF/serum ratio for albumin and IgG was calculated. The electrophoretic pattern of CSF was examined by isoelectric focusing and that of plasma by electrophoresis.

Results. Cell counts. Table 1 lists the number of mononuclear leucocytes, polymorphonuclear leucocytes, and red blood cells in CSF. Other laboratory data. Non-PPS specific laboratory data for all patients and controls are given in Table 2: plasma IgG-iridex; protein content of CSF; activation of the complement system by C3–C4 in plasma; presence of same oligoclonal bands in plasma and CSF; damage to the blood brain barrier.

Twelve out of 13 PPS patients had a normal blood brain barrier. The remaining patient (no. 8) had a slightly impaired blood brain barrier confirmed by an elevated CSF/albumin ratio. None of the PPS patients or controls had elevated complement factors C3, C4 or C3d. Three of the PPS patients had oligoclonal IgG bands in their CSF accompanied by similar bands in their plasma. These oligoclonal bands were interpreted as being due to a non-specific inflammatory reaction. Six of the PPS patients but also two of the controls had slightly elevated levels of protein in CSF which is a sign of unspecific inflammation but none of them had an abnormal IgG index.

EXAMPLE 2

PPS-specific Data from PPS Patients. Comparison of Inflammation Marker Levels in PPS Patients and Healthy Volunteers The PPS group comprised patients no. 1–7 of Example 1 who were compared with the seven healthy volunteers of the same example.

PB and CSF of the patients was analyzed by in situ hybridization (ISH), which is a more specific method for detecting cytokine mRNA expression. ISH allows examination of cytokine mRNA expression in mononuclear cells from blood and CSF. ISH was performed according to Å. Dagerlind et al., Sensitive mRNA detection using unfixed tissue: combined radioactive and non-radioactive in situ hybridization histochemistry, *Histochemistry* 1992, 39–49. Aliquots containing $5·10^4$ PB lymphocytes or $10·10^3$ CSF cells were dried onto Super Frost microscope slides (Menzel-Glazer, Kebo Lab, Stockholm, Sweden).

A mixture of synthetic oligonucleotide probes (for expression of IL-4, IL-10, IFNγ, and TNFα, respectively; Scandinavian Gene Synthesis, Köping, Sweden) were labeled at their 3'-end with deoxyadenosine-5'-α-(thio)-triphosphate ($^{35}$S) (Dupont Scandinavia AB, Stockholm, Sweden) using terminal deoxynucleotidyl transferase (Amersham International, Little Chalfont, U.K.). A mixture of probes complimentary to the antisense strand of each cytokine was used as negative control. Hybridization was performed for 16–18 hours at 42° C. with $10^6$ CPM of labeled probe per 100 μl of hybridization mixture containing 50% formamide, 4×SSC buffer, 1×Denhart's solution (0.02% by weight each of polyvinylpyrrolidone (Sigma, Poole, U.K.), bovine serum albumin and Ficoll (Sigma), 1% sarcosyl (Sigma), 0.02M phosphate buffer pH 7.0, 10% dextran sulphate (Pharmacia, Uppsala, Sweden), 500 μg/ml heat denaturated salmon sperm DNA (Sigma) and 200 mM dithiothreitol (Sigma). Upon hybridization, the slides were rinsed four times for 15 min at 55° C. in 1×SSC and dehydrated by applying an ethanol gradient (65% to 95%) and air dried. The slides were immersed in Kodak NTB2 emulsion (Kodak) diluted 1:1 with distilled water at a temperature of 4° C. for 2 weeks. After developing in Kodak D 19 developer, the slides were stained with cresyl violet (Sigma) and mounted with ENTELLAN™ (Merck, Darmstadt, Germany). The slides were coded and evaluated by light microscopy. Cells with more than 10 autoradiographic silver grains were regarded as cytokine mRNA expressing cells. The ISH analysis was carried out with the same probes at the same time for both groups.

Statistical analysis. Differences in cell numbers for each cytokine recorded in PPS patients and healthy controls were tested for significance with a non-parametric Wilcoxon signed-rank test.

Results. PPS specific data obtained in these experiments are listed in Tables 3–6.

All except one (patient no. 4) of the seven PPS patients had abnormal values of IL-4 producing T-cells in CSF (Table 3) but none of the controls. Three of the PPS patients had abnormal values of IL-4 producing T-cells in CSF (Table 4). All patients except one (patient no. 4) had abnormal values of IFNγ producing cells in CSF (Table 5) but only one control (volunteer no. 2) had an abnormal value. Four of the PPS patients had abnormal values of TFNα in CSF (Table 6).

Conclusions. In comparison with the controls there were significantly ($p<0.02$) higher levels of IL-4 in the PPS group, whereas IL-10, INFγ and TNFα showed a tendency, albeit not a statistically significant one, towards higher levels. The elevated levels of mRNA-expressing MNC for cytokines in CSF are not paralleled in PB. Healthy subjects do not have increased levels of mRNA expressing MNCs for cytokines in CSF. Therefore IL-4 in CSF is the marker of preference for PPS. The results indicate that IL-10, INFγ and TNFα also are useful PPS markers.

EXAMPLE 3

Analgesia Produced in Two PPS Patients by Intravenous Administration of Gamma-globulin Two patients (women, 79 and 67 years of age) with a documented polio infection earlier in their life and who met the PPS criteria according to Halstead and Rossi and the criteria of Post-Polio muscle dysfunction according to Borg were treated with intravenous gamma-globulin (GAMMAGARD™ Baxter). The older patient received a single dose of 20 g gamma-globulin whereas the younger patient received three consecutive daily doses of 30 g each. The indication for which they were treated was progressing neuromuscular dysfunction and pain increasing over time. The effect of treatment was evaluated two weeks after start. Both patients reported reduced pain. One of the patients showed improved neuromuscular function when tested by means of quantitative assessment of muscular force.

EXAMPLE 4

Gamma-globulin Compositions for Intravenous, Intramuscular, and Subcutaneous Administration for Treatment of PPS Useful 'normal' gamma-globulin compositions are known in the art. The composition used in Example 3 is GAMMAGARD™ S/D (Baxter Medical AB, Kista, Sweden). It is produced from plasma by a slightly modified Coin alcohol fractionation technique from plasma collected from North American donors. It contains a wide spectrum of 'normal' IgG antibodies of which at least 98% are in monomer or dimer form. GAMMAGARD™ S/D is reconstituted from freeze dried substance comprising IgG, glycin, sodium chloride, glucose monohydrate, human albumin, and polyethylene glycol by addition of water as pharmaceutical carrier. Gamma-globulin compositions may also come in form of aqueous solutions, such as GAMMANORM™ (Pharmacia & Upjohn Sverige AB, Stockholm; from plasma collected from Scandinavian donors) for intramuscular or subcutaneous administration. It is advantageous to provide single dose syringes pre-filled with gamma-globulin, in particular for self-treatment of PPS.

TABLE 1

Total count+ blood cells in cerebrospinal fluid of Post Polio Syndrome Patients

| Patient no. | Mononuclear leucocytes | Polymorphonuclear leucocytes | Red blood cells* |
|---|---|---|---|
| 01 | 2 | 0 | 8 |
| 02 | 4 | 0 | 14 |
| 03 | 0 | 0 | 87 |
| 04 | 0 | 0 | 0 |
| 05 | 0 | 2 | 450 |
| 06 | 0 | 0 | 179 |
| 07 | 4 | 2 | 27 |
| 08 | 2 | 0 | 452 |
| 09 | 0 | 0 | 14 |
| 10 | 0 | 0 | 261 |
| 11 | 0 | 0 | 3 |
| 12 | 8 | 4 | 8250 |
| Controls** | | | |
| 01 | 0 | 0 | 0 |
| 02 | 0 | 0 | 3 |
| 03 | 2 | 0 | 0 |
| 04 | 4 | 0 | 0 |
| 05 | 0 | 0 | 0 |
| 06 | 1 | 0 | 14 |
| 07 | 1 | 0 | 0 |

*The presence of red blood cells in CSF is due to the sample drawn from CNF for blood cell counts was the first upon lumbar puncture. In persons with a history of polio lumbar puncture often is a problem due to severe scoliosis; the bleeding affects in particular the first few milliliters drawn.
**Controls are healthy control subjects.
+Cell counts are number of counted cells × $10^6$/l fluid.

TABLE 2

Laboratory data for PPS patients and controls

| Patient # sex/age | IgG-index | CSF-protein | C-activity | Electrophoresis | Barrier damage |
|---|---|---|---|---|---|
| 01 M-78 | 0.42 | 0.40 | 0 | yes | 0 |
| 02 F-58 | 0.52 | 0.38 | 0 | 0 | 0 |
| 03 F-57 | 0.42 | 0.38 | 0 | 0 | 0 |
| 04 M-37 | 0.45 | 0.34 | 0 | yes | 0 |
| 05 F-54 | 0.49 | 0.54 | 0 | 0 | 0 |
| 06 F-67 | 0.42 | 0.48 | 0 | 0 | 0 |
| 07 M-70 | 0.48 | 0.55 | 0 | yes | 0 |
| 08 M-68 | 0.47 | 0.77 | 0 | 0 | yes |
| 09 F-55 | 0.45 | 0.48 | 0 | 0 | 0 |
| 10 M-76 | 0.52 | 0.53 | 0 | 0 | 0 |
| 11 M-54 | 0.45 | 0.59 | 0 | 0 | 0 |
| 12 M-31 | 0.52 | 0.52 | 0 | 0 | 0 |
| 13 M-54 | 0.42 | 0.48 | 0 | 0 | 0 |
| Controls | | | | | |
| 01 F-44 | 0.53 | 0.50 | 0 | 0 | 0 |
| 02 M-72 | 0.44 | 0.61 | 0 | 0 | 0 |
| 03 F-43 | 0.46 | 0.31 | 0 | 0 | 0 |
| 04 M-45 | 0.76 | 0.72 | 0 | 0 | yes |
| 05 M-23 | 0.46 | 0.21 | 0 | 0 | 0 |
| 06 F-47 | 0.62 | 0.38 | 0 | 0 | 0 |
| 07 F-52 | 0.52 | 0.49 | 0 | 0 | 0 |

Controls are healthy control subjects. Cell counts are number of counted cells×$10^6$/l fluid. IgG-index reference range: 0.35–0.70. CSF-protein=protein content of CSF; reference range: 0.12–0.50 g/liter. C-activity=analysis of activation of the complement system by C3–C4. Electrophoresis=plasma electrophoresis; isoelectric focussing of CSF; 0=no pathological pattern in plasma or CSF. Yes=similar oligoclonal bands present in plasma and CSF. Barrier damage: signs of slight damage to the blood brain barrier.

TABLE 3

Number of mononuclear leukocytes (MNC) expressing mRNA coding for IL-4 per liter of fluid ×$10^5$

| Patient no. | PPS PB* | PPS CSF** | Control PB† | Control CSF‡ |
|---|---|---|---|---|
| 01 | 0 | 240 | 2 | 0 |
| 02 | 2 | 200 | 0 | 0 |
| 03 | 2 | 140 | 4 | 0 |
| 04 | 0 | 0 | 0 | 0 |
| 05 | 4 | 100 | 0 | 0 |
| 06 | 4 | 80 | 0 | 0 |
| 07 | 6 | 140 | 0 | 0 |

*MNC in peripheral blood of PPS patients. **MNC in CSF of PPS patients. †MNC in peripheral blood of controls. ‡MNC in CSF of controls. The non-parametric Wilcoxons' signed rank test shows statistically significant differences between cell counts in CSF expressing mRNA coding for IL-4 ($p < 0.05$).

TABLE 4

Number of mononuclear leukocytes (MNC) expressing mRNA coding for IL-10 per liter of fluid ×$10^5$

| Patient no. | PPS PB* | PPS CSF** | Control PB† | Control CSF†† |
|---|---|---|---|---|
| 01 | 0 | 0 | 0 | 0 |
| 02 | 10 | 140 | 8 | 0 |
| 03 | 2 | 20 | 6 | 0 |
| 04 | 2 | 0 | 4 | 0 |

TABLE 4-continued

Number of mononuclear leukocytes
(MNC) expressing mRNA coding for IL-10 per liter of fluid
$\times 10^5$

| Patient no. | PPS PB* | PPS CSF** | Control PB† | Control CSF†† |
|---|---|---|---|---|
| 05 | 4 | 0 | 2 | 0 |
| 06 | 4 | 0 | 2 | 0 |
| 07 | 6 | 20 | 2 | 0 |

*MNC in peripheral blood of PPS patients. **MNC in CSF of PPS patients. †MNC in peripheral blood of controls. ††MNC in CSF of controls.

TABLE 5

Number of mononuclear leukocytes
(MNC) expressing mRNA coding for IFNγ per liter of fluid
$\times 10^5$

| Patient no. | PPS PB* | PPS CSF** | Control PB† | Control CSF†† |
|---|---|---|---|---|
| 01 | 0 | 100 | 0 | 0 |
| 02 | 2 | 160 | 4 | 40 |
| 03 | 2 | 0 | 4 | 0 |
| 04 | 0 | 40 | 0 | 0 |
| 05 | 2 | 40 | 2 | 0 |
| 06 | 6 | 20 | 0 | 0 |
| 07 | 2 | 40 | 2 | 0 |

*MNC in peripheral blood of PPS patients. **MNC in CSF of PPS patients. †MNC in peripheral blood of controls. ††MNC in CSF of controls.

TABLE 6

Number of mononuclear leukocytes
(MNC) expressing mRNA coding for TNFα per liter of fluid
$\times 10^5$

| Patient no. | PPS PB* | PPS CSF** | Control PB† | Control CSF†† |
|---|---|---|---|---|
| 01 | 4 | 100 | 4 | 0 |
| 02 | 20 | 200 | 0 | 0 |
| 03 | 8 | 40 | 0 | 0 |
| 04 | 4 | 0 | 0 | 0 |
| 05 | 2 | 0 | 4 | 0 |
| 06 | 0 | 0 | 2 | 0 |
| 07 | 4 | 60 | 0 | 0 |

*MNC in peripheral blood of PPS patients. **MNC in CSF of PPS patients. †MNC in peripheral blood of controls. ††MNC in CSF of controls.

What is claimed is:

1. A method for treating a patient suffering from Post-Polio Syndrome (PPS) comprising the intravenous, intramuscular or subcutaneous administration of a pharmacologically effective amount of normal gamma-globulin.

2. The method of claim 1, wherein the gamma-globulin is administered in an amount of from 0.01 g/kg/day to 1.0 g/kg/day.

3. The method of claim 2, wherein the treatment is an once daily treatment for a treatment period of from 1 to 6 days.

4. The method of claim 2, wherein the treatment is a once daily treatment for a treatment period of at least a week.

5. The method of claim 2, wherein the treatment comprises daily treatment during a first treatment period and a second treatment period, said treatment periods being interrupted by a treatment-free period.

6. The method of claim 5, wherein the treatment-free period is longer than first and second treatment periods in combination.

7. The method of claim 1, wherein the gamma-globulin is administered in form of single doses comprising from 0.5 g to 50.0 g.

8. The method of claim 7, wherein the gamma-globulin is administered in combination with an aqueous pharmaceutically acceptable carrier.

9. The method of claim 8, wherein the gamma-globulin is administered in an amount of from 0.1 g/kg/day to 0.4 g/kg/day.

10. The method of claim 9, wherein the administration is intravenous.

11. The method of claim 7, wherein said single dose is dispensed from a disposable syringe.

12. The method of claim 1, wherein the administration is intravenous.

* * * * *